(12) United States Patent
Thirasak et al.

(10) Patent No.: US 10,479,743 B2
(45) Date of Patent: Nov. 19, 2019

(54) PROCESS FOR THE SEPARATION OF ETHYLBENZENE

(71) Applicant: SCG CHEMICALS COMPANY LIMITED, Bangkok Metropolis (TH)

(72) Inventors: Attapong Thirasak, Rayong (TH); Alisa Kammafoo, Rayong (TH); Arnat Prombunglum, Rayong (TH)

(73) Assignee: SCG Chemicals Company Limited, Bangkok (TH)

( * ) Notice: Subject to any disclaimer, the term of this patent is extended or adjusted under 35 U.S.C. 154(b) by 113 days.

(21) Appl. No.: 15/506,363

(22) PCT Filed: Sep. 4, 2015

(86) PCT No.: PCT/TH2015/000056
§ 371 (c)(1),
(2) Date: Feb. 24, 2017

(87) PCT Pub. No.: WO2016/036326
PCT Pub. Date: Mar. 10, 2016

(65) Prior Publication Data
US 2017/0240490 A1    Aug. 24, 2017

(30) Foreign Application Priority Data

Sep. 5, 2014    (EP) .................................. 14003073

(51) Int. Cl.
| | | |
|---|---|---|
| *C07C 7/08* | (2006.01) | |
| *C07C 7/06* | (2006.01) | |
| *B01D 3/36* | (2006.01) | |
| *B01D 3/40* | (2006.01) | |
| *B01D 3/38* | (2006.01) | |

(52) U.S. Cl.
CPC .................. *C07C 7/08* (2013.01); *B01D 3/36* (2013.01); *B01D 3/38* (2013.01); *B01D 3/40* (2013.01); *C07C 7/06* (2013.01)

(58) Field of Classification Search
CPC ......................... B01D 3/36–40; C07C 7/05–08
See application file for complete search history.

(56) References Cited

U.S. PATENT DOCUMENTS

| | | | |
|---|---|---|---|
| 3,105,017 A | | 9/1963 | Amir et al. |
| 3,591,490 A | * | 7/1971 | Muller et al. ............. C07C 7/08 208/313 |

(Continued)

FOREIGN PATENT DOCUMENTS

| | | |
|---|---|---|
| JP | S49-070930 | 7/1974 |
| JP | H11509868 A | 8/1999 |

(Continued)

OTHER PUBLICATIONS

International Search Report for International Patent Application No. PCT/TH2015/000056, dated Jan. 27, 2016 (3 pages).

(Continued)

*Primary Examiner* — Renee Robinson
(74) *Attorney, Agent, or Firm* — Dorsey & Whitney LLP

(57) ABSTRACT

Ethylbenzene can be separated from a C8 aromatics mixture containing ethylbenzene and a close boiling compound by extractive distillation using an extractive agent comprising a mixture of a chlorinated aromatic compound and another compound selected from furandione derivatives and organic nitriles.

14 Claims, 1 Drawing Sheet

(56) References Cited

U.S. PATENT DOCUMENTS

| | | | |
|---|---|---|---|
| 4,292,142 A | | 9/1981 | Berg et al. |
| 4,299,668 A | | 11/1981 | Berg |
| 4,959,128 A | | 9/1990 | Berg |
| 5,849,982 A | * | 12/1998 | Lee ........................ B01D 3/322 |
| | | | 585/833 |

FOREIGN PATENT DOCUMENTS

| | | |
|---|---|---|
| RU | 2125977 C1 | 2/1999 |
| SU | 1696416 A1 | 12/1991 |
| WO | 9744298 A1 | 11/1997 |

OTHER PUBLICATIONS

Written Opinion of the International Searching Authority for International Patent Application No. PCT/TH2015/000056, dated Jan. 27, 2016 (5 pages).
Search Report for Russian Patent Application No. 2017111205, dated Sep. 28, 2018, with English translation (4 pages).
First Examination Report for Indian Application No. 201717006708, dated Jan. 4, 2019 (5 pages).

\* cited by examiner

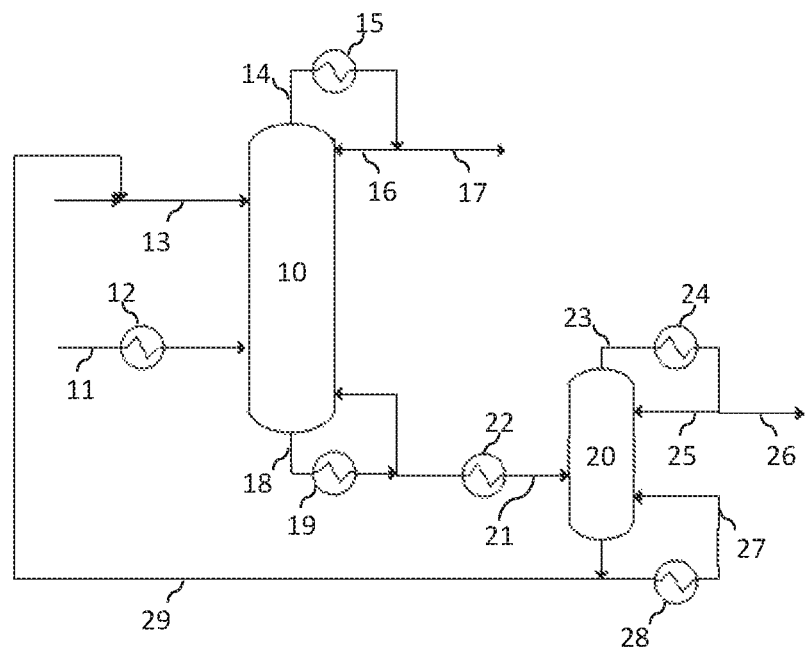

PROCESS FOR THE SEPARATION OF ETHYLBENZENE

TECHNICAL FIELD OF INVENTION

The present invention relates to a process for separation of ethylbenzene from a mixture comprising C8 aromatics by extractive distillation.

BACKGROUND OF INVENTION

Separation of close boiling compounds usually requires a process more sophisticated than conventional distillation. Extractive distillation is one of the techniques developed for this purpose. It has been applied in industrial processes, and is becoming a more and more important separation method in petrochemical industries. The main characteristic of extractive distillation is that one new solvent with high boiling-point, i.e. extractive agent, is added to the components to be separated, so as to increase the relative volatility of the targeted components. Relative volatility is a measure of the differences between the vapor pressure of the more volatile component and the vapor pressure of the less volatile component in a liquid mixture. It indicates degree of separability of two components in the mixture. Besides altering the relative volatility, the extractive agent should also be easily separated from the distillation products, that is, high boiling point difference between the extractive agent and the components to be separated is desirable. The extractive agent plays an important role in the design of extractive distillation. Therefore, selection of suitable extractive agent is essential to ensure an effective and economical design.

Ethylbenzene is a hydrocarbon compound with high commercial utilization and value. It is majorly used to produce styrene which is an intermediate for polystyrene production. Ethylbenzene may be obtained from alkylation reaction between benzene and ethylene. An alternative way for producing ethylbenzene is to recover it from a hydrocarbon mixture containing ethylbenzene which is generally produced as a byproduct stream from several petrochemical processes. The hydrocarbon mixture containing ethylbenzene usually also contain one or more hydrocarbon compound with boiling point close to boiling point of ethylbenzene, especially C8 aromatic isomers.

Attempts have been made to separate ethylbenzene from a hydrocarbon mixture. A GB patent number 1,198,592 describes a process for separating C8 aromatic isomers using a single polyfunctional distillation column. The distillation is carried out in a multiplate column having at least 250 and preferably 365 trays and a reflux ratio from 100 to 250:1 in order to achieve high purity ethylbenzene product. A large distillation column is known to have high cost of construction and high reflux rate leads to high energy consumption during operation.

A U.S. Pat. No. 3,105,017 describes a method for separating a C8 aromatic hydrocarbon mixture by distilling said mixture in the presence of a compound containing a single benzene ring substituted on the ring in at least two positions with a chloro group under conditions to separate a fraction enriched with ethylbenzene. However, this method still does not provide very high separation efficiency.

A U.S. Pat. No. 4,299,668 describes a method for separating ethylbenzene from para-xylene and/or meta-xylene in a rectification column in the presence of an extractive agent comprising pentachlorophenol as a main component mixed with one or more other compounds. Pentachlorophenol appears as white crystalline solid at room temperature with high melting point, therefore requires an additional step and energy for dissolving of pentachlorophenol in a suitable solvent before using as an extractive agent. Moreover, pentachlorophenol is extremely toxic to humans from acute ingestion and inhalation exposure.

BRIEF DESCRIPTION OF DRAWING

FIG. 1 is a process for separation of ethylbenzene from a C8 aromatics mixture according to an embodiment of the present invention.

SUMMARY OF INVENTION

It has now surprisingly been found that the separation efficiency for the separation of ethylbenzene by extractive distillation of an ethylbenzene containing mixture can be improved by distilling the mixture in the presence of an extractive agent which comprises a chlorinated aromatic compound and an organic compound selected from furandione derivatives and organic nitriles.

The present invention therefore provides an improved process for separation of ethylbenzene from a mixture comprising C8 aromatics which comprises distilling the mixture comprising C8 aromatics in the presence of an extractive agent wherein the extractive agent comprises a chlorinated aromatic compound and an organic compound selected from furandione derivatives and organic nitriles.

In the following the mixture comprising C8 aromatics is also denoted as "C8 aromatics mixture".

The process according to the present invention exhibits effective process for producing high yields of commercially pure ethylbenzene and mixed xylene products.

DETAILED DESCRIPTION OF INVENTION

In a preferred embodiment of the process of the invention, the at least one organic compound is selected from
a) furandione derivates according to the following formula:

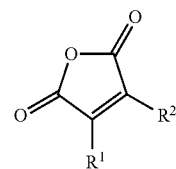

wherein $R^1$ and $R^2$ independently from each other are H or an organic group, wherein $R^1$ and $R^2$ may also be linked to each other to form a ring structure, preferably, $R^1$ and $R^2$ independently are H or a hydrocarbon group wherein $R^1$ and $R^2$ may also be linked to each other to form a ring structure, more preferably $R^1$ and $R^2$ are hydrocarbons and are linked to each other to form a ring structure, still more preferably $R^1$ and $R^2$ are hydrocarbons and are linked to each other to form a ring structure so that an aromatic system is formed fused to the furan ring, and most preferably the furandione compound is phthalic anhydride,
and
b) organic nitriles according to the following formula:

wherein R is an organic group, preferably R is a hydrocarbon group, more preferably R is an aliphatic or aromatic hydrocarbon group, still more preferably R is a C1 to C12 aliphatic or aromatic hydrocarbon group, and most preferably the organic nitrile is acetonitrile or benzonitrile.

Thus, in a particularly preferred embodiment, the at least one organic compound is selected from phthalic anhydride, acetonitrile and benzonitrile.

The C8 aromatics mixture can be obtained from various petrochemical processes. Preferably, the C8 aromatics mixture is obtained from aromatic recovery process of either steam crackers or refineries where the C8 aromatic cut majorly contains ethylbenzene with some other compounds in a close boiling range. Different sources provide different compositions of the C8 aromatics mixture stream.

In one embodiment, the C8 aromatics mixture comprises a xylene isomer selected from ortho-xylene, meta-xylene, para-xylene or a mixture thereof.

In a particular embodiment, the C8 aromatics mixture may further comprise benzene, toluene, styrene, C8 non-aromatic compounds, C9 non-aromatic compounds or a mixture thereof. More suitably, the C8 aromatics mixture comprises less than 5 percent by weight of nonaromatic compounds in order to obtain high purity ethylbenzene product, e.g. higher than 90 wt % purity, preferably higher than 99 wt % purity.

The process of the present invention is applicable with the CS aromatics mixture with a wide range of ethylbenzene content. However, very low ethylbenzene content may cause the process to be less economically attractive.

In one embodiment, the C8 aromatics mixture comprises 5 to 99 percent by weight of ethylbenzene, preferably 20 to 95 percent by weight of ethylbenzene, more preferably 30 to 85 percent by weight of ethylbenzene.

Furthermore, in one embodiment of the present invention, the ethylbenzene product comprises more than 80 percent by weight of ethylbenzene, preferably more than 90 percent by weight of ethylbenzene, more preferably more than 95 percent by weight of ethylbenzene, and still more preferably more than 99 percent by weight of ethylbenzene.

The extractive agent employed in the present invention comprises a chlorinated aromatic compound and an organic compound selected from furandione derivatives and organic nitriles in any of the above described embodiments, preferably selected from phthalic anhydride, acetonitrile and benzonitrile. These compounds were chosen based on many experimental results and careful consideration. The extractive agent should increase relative volatility of components present in the C8 aromatics mixture as much as possible. At the same time, the extractive agent should be able to be recovered and recycled in order for the process to be more economically attractive.

In one embodiment, the chlorinated aromatic compound comprises, preferably consists of, chlorinated benzene selected from chlorobenzene, dichlorobenzenes, trichlorobenzenes, tetrachlorobenzenes, pentachlorobenzene and benzene hexachloride, preferably trichlorobenzenes.

In a specific embodiment, the chlorinated aromatic compound comprises, preferably consists of, trichlorobenzene selected from 1,2,3-trichlorobenzene, 1,2,4-trichlorobenzene and 1,3,5-trichlorobenzene, preferably 1,2,4-trichlorobenzene.

Any proportional mixing ratio of components in the extractive agent can be employed. A suitable composition may be used to achieve a more efficient separation. In a preferred embodiment, the extractive agent comprises 1 to 50 percent by weight of the organic compound, preferably 1 to 30 percent by weight of the organic compound, and still more preferably from 2 to 25 percent by weight of the organic compound.

The amount of the extractive agent used should be enough to improve the relative volatility of the C8 aromatics mixture throughout the distillation column. In a particular embodiment, the weight ratio of the extractive agent to the C8 aromatics mixture is in the range of 0.2:1 to 20:1, preferably 0.5:1 to 12:1, more preferably 1:1 to 10:1.

The process according to the present invention can be conducted in either anhydrous or hydrated environment. To create a hydrated environment, water or steam is added to the process of invention. Thus, in one embodiment in the process of the invention distilling the C8 mixture is carried out in the presence of water or steam.

Preferably, in this embodiment, 0.01 to 10 parts by weight of water per 100 parts by weight of the extractive agent are added in the process of invention, more preferably 0.05 to 10 parts by weight of water per 100 parts by weight of the extractive agent are added, and most preferably 0.5 to 5 parts by weight of water per 100 parts by weight of the extractive agent are added.

In one preferred embodiment, the extractive agent is recovered and recycled to make the process more economically attractive.

An exemplary procedure for carrying out the process according to one embodiment of this invention will be explained hereinunder by reference to FIG. 1.

FIG. 1 is a process for separation of ethylbenzene from a C8 aromatics mixture according to an embodiment of the present invention. In the particular embodiment wherein the C8 aromatics mixture comprises ethylbenzene and at least one xylene isomer selected from ortho-xylene, meta-xylene, and para-xylene, the separation can be carried out by introducing the C8 aromatics mixture to a distillation column 10 through conduit 11. The internal of the distillation column 10 can be variously chosen to get a desired efficiency, for example the distillation column 10 may be filled with a number of packed beds or trays. The temperature of the C8 aromatics mixture may be adjusted as needed by controlling a heat exchanger 12. An extractive agent comprising a chlorinated aromatic compound and an organic compound selected from a furandione derivative and an organic nitrile, preferably selected from phthalic anhydride, acetonitrile and benzonitrile is simultaneously introduced to the distillation column 10 through conduit 13. The selected components are premixed to a desired composition of the extractive agent before it is introduced to the distillation column 10. Alternatively, predeteiniined amount of each components of the extractive agent may be fed separately into the distillation column 10. When a hydrated environment is desired, a predetermined amount of water or steam can be premixed into the extractive agent composition or separately fed into the distillation column 10. The extractive agent will preferentially form a higher boiling point mixture with the at least one xylene isomer and be distilled down the distillation column 10, whereas the lighter boiling ethylbenzene which has no or lower affinity with the extractive agent will be distilled up the distillation column 10.

An overhead product enriched with ethylbenzene is withdrawn from the upper part of the distillation column 10 through conduit 14. This overhead product stream can be completely passed to storage. In a more general case, this overhead product is condensed in a condenser 15. A portion of the condensed overhead stream is returned to the distillation column 10 as reflux through conduit 16, while another portion of the condensed overhead product is collected as an ethylbenzene product or passed to other processing units through conduit 17. In one embodiment of the present invention, the ethylbenzene product comprises more than 80 percent by weight of ethylbenzene, preferably more than 90 percent by weight of ethylbenzene, more preferably more than 95 percent by weight of ethylbenzene, and most preferably more than 99 percent by weight of ethylbenzene.

A bottom product comprising the extractive agent and at least one xylene isomer is withdrawn from a lower portion of the distillation column 10 through conduit 18. This bottom product can be passed to storage or used in other processes. Preferably, a portion of the bottom product is heated in a heat exchanger 19 and returned to the distillation column 10 and another portion of the bottom product is passed to a recovery column 20 through conduit 21. Temperature of the bottom product passing to the recovery column 20 can be appropriately adjusted by controlling a heat exchanger 22. Operating condition of the recovery column 20 is preferably adjusted to effectuate separation between the extractive agent and the at least one xylene isomer.

An overhead product predominantly comprising the at least one xylene isomer is withdrawn from an upper portion of the recovery column 20 through conduit 23. Preferably, this overhead product can be at least partially condensed in a condenser 24. A portion of the condensed overhead product is returned to the recovery column 20 as reflux through conduit 25 and another portion of the condensed overhead product is collected as a mixed xylenes product through conduit 26.

A bottom product predominantly comprising the extractive agent is withdrawn from a lower portion of the recovery column 20 through conduit 27. Preferably, a portion of this bottom product is heated in a heat exchanger 28 and returned to the recovery column 20 and another portion of this bottom product is recycled to the distillation column 10 through conduit 29.

Additional equipment such as heat exchanger, pump or compressor may be added to any appropriate location of the process system in order to properly adjust condition of the process. Suitable dimension and configuration of all equipment in the process can be modified by those having ordinary skills in the art to match with the exact composition of the hydrocarbon mixture, the extractive agent and specific operating conditions employed.

EXAMPLES

Example 1

Separation efficiencies of different extractive agent were determined. Experiments were done in a vapor-liquid equilibrium determination apparatus (FISCHER® VLE 602) by introducing a C8 hydrocarbon feed mixture containing 60 wt % of ethylbenzene, 10 wt % of para-xylene, 20 wt % of meta-xylene and 10 wt % of ortho-xylene and a selected extractive agent into the apparatus at an extractive agent to feed ratio of 5:1 by weight. Temperature was gradually increased until vapor-liquid equilibrium was achieved. The pressure was 500 mbar. Different extractive agents were tested for comparison purpose. Test results are shown in Table 1.

Relative volatility values shown in Table 1 were calculated by the following equation (1).

$$\alpha_{i,j} = \frac{y_i/x_i}{y_j/x_j} \quad (1)$$

Wherein
$\alpha_{i,j}$ is a relative volatility between ethylbenzene and p-xylene,
$y_i$ is vapor mass fraction of ethylbenzene,
$x_i$ is liquid mass fraction of ethylbenzene,
$y_j$ is vapor mass fraction of p-xylene, and
$x_j$ is liquid mass fraction of p-xylene.

TABLE 1

| Extractive agent | Relative volatility |
| --- | --- |
| None | 1.080 |
| 100 wt % 1,2,4-trichlorobenzene | 1.150 |
| 95 wt % 1,2,4-trichlorobenzene and 5 wt % phthalic anhydride | 1.154 |
| 95 wt % 1,2,4-trichlorobenzene and 5 wt % acetonitrile | 1.180 |
| 95 wt % 1,2,4-trichlorobenzene and 5 wt % benzonitrile | 1.158 |
| 95 wt % 1,2,4-trichlorobenzene and 10 wt % acetonitrile | 1.200 |
| 95 wt % 1,2,4-trichlorobenzene, 5 wt % acetonitrile, and 1 part by weight of water per 100 parts of the extractive agent | 1.257 |

Example 2

The effect of different extractive agent to feed ratios were determined using the same apparatus and test method as described in Example 1 but with the selected extractive agent being 95 wt % 1,2,4-trichlorobenzene and 5 wt % acetonitrile, and the extractive agent to feed ratio being varied from 1:1 to 5:1 by weight. The results are shown in Table 2.

TABLE 2

| Extractive agent to feed ratio (wt:wt) | Relative volatility |
| --- | --- |
| 1:1 | 1.152 |
| 3:1 | 1.170 |
| 5:1 | 1.180 |

The invention claimed is:

1. A process for separation of ethylbenzene from a mixture comprising C8 aromatics comprising:
   distilling the mixture comprising C8 aromatics in the presence of an extractive agent;
   wherein the extractive agent comprises a chlorinated aromatic compound and an organic compound selected from the group consisting of furandione derivatives and organic nitriles;
   wherein the extractive agent comprises 5 to 20 percent by weight of the organic compound; and
   wherein a weight ratio of the extractive agent to the mixture comprising C8 aromatics is in the range of 0.2:1 to 20:1.

2. The process according to claim 1 wherein the organic compound is selected from the group consisting of phthalic anhydride, acetonitrile, benzonitrile, and mixtures thereof.

3. The process according to claim 1 or 2 wherein the mixture comprising C8 aromatics comprises a xylene isomer selected from the group consisting of ortho-xylene, meta-xylene, para xylene, and mixtures thereof.

4. The process according to claim 1 or 2 wherein the chlorinated aromatic compound comprises a chlorinated benzene selected from the group consisting of dichlorobenzene, trichlorobenzene, tetrachlorobenzene, pentachlorobenzene and benzene hexachloride.

5. The process according to claim 4 wherein the trichlorobenzene is selected from the group consisting of 1,2,3-trichlorobenzene, 1,2,4-trichlorobenzene and 1,3,5-trichlorobenzene.

6. The process according to claim 1 or 2 wherein the weight ratio of the extractive agent to the mixture comprising C8 aromatics is in the range of 0.5:1 to 12:1.

7. The process according to claim 1 wherein distilling the mixture comprising C8 aromatics is carried out in the presence of water or steam.

8. The process according to claim 7 wherein distilling the mixture comprising C8 aromatics is carried out in the presence of 0.01 to 10 parts by weight of water or steam per 100 parts by weight of the extractive agent.

9. The process according to claim 7 wherein distilling the mixture comprising C8 aromatics is carried out in the presence of 0.5 to 10 parts by weight of water or steam per 100 parts by weight of extractive agent.

10. The process according to claim 1 or 2 wherein the extractive agent is recovered and recycled.

11. The process according to claim 1 or 2 wherein the extractive agent comprises from 5 to 10 percent by weight of the organic compound.

12. The process according to claim 1 or 2 wherein the weight ratio of the extractive agent to the mixture comprising C8 aromatics is in the range of 1:1 to 10:1.

13. The process according to claim 1 wherein the extractive agent comprises from 5 to 15 percent by weight of the organic compound.

14. The process according to claim 1 wherein a weight ratio of the extractive agent to the mixture comprising C8 aromatics is in the range of 5:1 to 10:1.

* * * * *